(12) United States Patent
Beer et al.

(10) Patent No.: US 9,939,170 B2
(45) Date of Patent: Apr. 10, 2018

(54) METHODS AND COMPOSITIONS FOR RAPID THERMAL CYCLING

(71) Applicant: Lawrence Livermore National Security, LLC, Livermore, CA (US)

(72) Inventors: Neil Reginald Beer, Pleasanton, CA (US); William J. Benett, Livermore, CA (US); James M. Frank, Lewisville, TX (US); Joshua R. Deotte, Southlake, TX (US); Christopher Spadaccini, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 405 days.

(21) Appl. No.: 14/834,805

(22) Filed: Aug. 25, 2015

(65) Prior Publication Data

US 2015/0352553 A1 Dec. 10, 2015

Related U.S. Application Data

(63) Continuation of application No. 13/267,767, filed on Oct. 6, 2011, now Pat. No. 9,170,028.
(Continued)

(51) Int. Cl.
*F24H 1/10* (2006.01)
*F24H 1/00* (2006.01)
(Continued)

(52) U.S. Cl.
CPC ............. *F24H 1/00* (2013.01); *B01L 7/52* (2013.01); *B01L 7/54* (2013.01); *C12M 29/00* (2013.01);
(Continued)

(58) Field of Classification Search
CPC ............. F24H 1/10; H05B 3/78; F28D 7/00
(Continued)

(56) References Cited

U.S. PATENT DOCUMENTS 3,888,303 A * 6/1975 Skala ................... A47J 27/17
165/104.14
5,498,392 A * 3/1996 Wilding ................ B01D 61/18
422/400
(Continued)

FOREIGN PATENT DOCUMENTS

WO WO 2008/070198 6/2008
WO WO 2009/094061 7/2009
(Continued)

OTHER PUBLICATIONS

Amendment dated Oct. 15, 2010 for EP Patent Application No. 08871258.3, filed Nov. 17, 2010.
(Continued)

*Primary Examiner* — Michael Laflame, Jr.
(74) *Attorney, Agent, or Firm* — Fenwick & West, LLP

(57) ABSTRACT

The rapid thermal cycling of a material is targeted. A microfluidic heat exchanger with an internal porous medium is coupled to tanks containing cold fluid and hot fluid. Fluid flows alternately from the cold tank and the hot tank into the porous medium, cooling and heating samples contained in the microfluidic heat exchanger's sample wells. A valve may be coupled to the tanks and a pump, and switching the position of the valve may switch the source and direction of fluid flowing through the porous medium. A controller may control the switching of valve positions based on the temperature of the samples and determined temperature thresholds. A sample tray for containing samples to be thermally cycled may be used in conjunction with the thermal cycling system. A surface or internal electrical heater may aid in (Continued)

heating the samples, or may replace the necessity for the hot tank.

20 Claims, 9 Drawing Sheets

Related U.S. Application Data

(60) Provisional application No. 61/390,383, filed on Oct. 6, 2010, provisional application No. 61/390,415, filed on Oct. 6, 2010, provisional application No. 61/390,425, filed on Oct. 6, 2010, provisional application No. 61/390,433, filed on Oct. 6, 2010, provisional application No. 61/390,441, filed on Oct. 6, 2010, provisional application No. 61/390,452, filed on Oct. 6, 2010, provisional application No. 61/512,393, filed on Jul. 27, 2011.

(51) Int. Cl.
    H05B 3/78    (2006.01)
    C12M 1/34    (2006.01)
    C12M 1/02    (2006.01)
    C12M 1/00    (2006.01)
    C12M 1/36    (2006.01)
    B01L 7/00    (2006.01)

(52) U.S. Cl.
    CPC ............ *C12M 41/12* (2013.01); *C12M 41/18* (2013.01); *C12M 41/48* (2013.01); *B01L 2200/0689* (2013.01); *B01L 2200/12* (2013.01); *B01L 2300/0829* (2013.01); *B01L 2300/1805* (2013.01); *B01L 2300/1822* (2013.01); *B01L 2300/1827* (2013.01); *F24H 1/10* (2013.01)

(58) Field of Classification Search
    USPC ......... 392/485–490, 496; 435/6, 91.2, 303.1, 435/288.4, 305.2, 809; 219/428, 430
    See application file for complete search history.

(56) References Cited

U.S. PATENT DOCUMENTS

| | | | |
|---|---|---|---|
| 5,504,007 A * | 4/1996 | Haynes | B01L 7/52 435/285.1 |
| 5,834,252 A | 11/1998 | Stemmer et al. | |
| 5,882,465 A | 3/1999 | McReynolds | |
| 6,018,616 A | 1/2000 | Schaper | |
| 6,418,276 B2 * | 7/2002 | Huang | F24H 9/2014 219/486 |
| 6,501,654 B2 | 12/2002 | O'Connor et al. | |
| 7,665,311 B2 | 2/2010 | Steffensen et al. | |
| 2002/0119535 A1 | 8/2002 | Slater et al. | |
| 2003/0165946 A1 | 9/2003 | Evans | |
| 2005/0282224 A1 | 12/2005 | Fouillet et al. | |
| 2006/0042785 A1 | 3/2006 | Werner et al. | |
| 2006/0094108 A1 | 5/2006 | Yoder et al. | |
| 2006/0191893 A1 * | 8/2006 | Weinfield | B01D 61/18 219/428 |
| 2008/0022647 A1 | 1/2008 | Jones et al. | |
| 2008/0166793 A1 | 7/2008 | Beer et al. | |
| 2008/0270030 A1 | 10/2008 | Copley et al. | |
| 2009/0226971 A1 | 9/2009 | Beer et al. | |
| 2009/0226972 A1 | 9/2009 | Beer et al. | |
| 2010/0091459 A1 | 4/2010 | Zhang | |

FOREIGN PATENT DOCUMENTS

| | | |
|---|---|---|
| WO | WO 2010/093249 | 8/2010 |
| WO | WO 2011/028924 | 3/2011 |

OTHER PUBLICATIONS

Beer, N.R. et al., "On-Chip Single-Copy Real-Time Reverse-Transcription PCR in Isolated Picoliter Droplets," *Anal. Chem.*, 2008, pp. 1854-1858, vol. 80, No. 6.
Beer, N.R. et al., "On-Chip, Real-time, Single-copy Polymerase Chain Reaction in Picoliter Droplets," *Anal. Chem.*, 2007, pp. 8471-8475, vol. 79.
European Patent Office, Communication Pursuant to Rules 161(1) and 162 EPC, European Patent Application No. 08871258.3, dated Sep. 8, 2010, two pages.
Finnzymes, Inc., "24-well and 96-well Piko Thermal Cyclers," Jun. 20, 2010, four pages. [Online] [Retrieved Jan. 24, 2012] Retrieved from the Internet <URL:http://web.archive.org/web/20100620081305/http://www.finnzymes.us/Piko/thermalcyclers.html.>.
Fujimoto, T. et al., "Novel High-Speed Real-Time PCR Method (Hyper-PCR): Results from Its Application to Adenovirus Diagnosis," *Jpn. J. Infect. Dis.*, 2010, pp. 31-35, vol. 63.
Griep, M.A. et al., "Kinetics of the DNA Polymerase *pyrococcus kodakaraensis*," *Chemical Engineering Science*, Jun. 1, 2006, pp. 3885-3892, vol. 61.
Khanafer, K. et al.,"Isothermal Surface Production and Regulation for High Heat Flux Applications Utilizing Porous Inserts," *International Journal of Heat and Mass Transfer*, 2001, pp. 2933-2947, vol. 44.
Kim, Y.H. et al., "Performance Evaluation of Thermal Cyclers for PCR in a Rapid Cycling Condition," *BioTechniques*, Apr. 2008, pp. 495-505, vol. 44.
Kiss, M. et al., "High-Throughput Quantitative PCR in Picoliter Droplets," *Anal. Chem.*, 2008, pp. 8975-8981, vol. 80, No. 23.
Ksiazek, T. et al.,"A Novel Coronavirus Associated with Severe Acute Respiratory Syndrome," *New England Journal of Medicine*, 2003, pp. 1953-1966, vol. 348, No. 20.
Lee, W.-G. et al., "Nano/Microfluidics for Diagnosis of Infectious Diseases in Developing Countries," *Advanced Drug Delivery Reviews*, 2010, pp. 449-457, vol. 62, No. 4-5.
Mahjoob, S. et al., "Rapid Microfluidic Thermal Cycler for Polymerase Chain Reaction Nucleic Acid Amplification," *International Journal of Heat and Mass Transfer*, 2008, pp. 2109-2122, vol. 51.
Maltezos, G. et al., "Thermal Management in Microfluidics Using Micro-Peltier Junctions," *Applied Physics Letters*, 2005, pp. 154105-1 to 154105-3, vol. 87.
Neuzil, P. et al., "Ultra fast miniaturized real-time PCR: 40 cycles in less than six minutes," *Nucleic Acids Res.*, 2006, vol. 34, No. 11, nine pages.
PCT International Preliminary Report of Patentability, PCT Application No. PCT/US2008/083728, dated Jul. 27, 2010, seven pages.
PCT International Search Report and Written Opinion, PCT Application No. PCT/US2008/083728, dated Jun. 2, 2009, ten pages.
Smiths Detection, "Bio-Seeq PLUS: Feature Highlights," 2012, two pages. [Online] [Retrieved Jan. 24, 2012] Retrieved from the Internet <URL:http://www.smithsdetection.com/Bio-Seeq_PLUS.>.
Terazono, H. et al., "Development of a High-Speed Real-Time Polymerase Chain Reaction System Using a Circulating Water-Based Rapid Heat-Exchange," *Japanese Journal of Applied Physics*, Jun. 2010, pp. 06GM05-1 to 06GM05-5, vol. 49, No. 6, Issue 2 of 2.
Tewhey, R. et al., "Microdroplet-based PCR enrichment for large-scale targeted sequencing," *Nature Biotechnology*, Nov. 2009, pp. 1025-1031, vol. 27, No. 11.
U.S. Office Action, U.S. Appl. No. 12/270,030, dated May 4, 2011, nine pages.
U.S. Office Action, U.S. Appl. No. 12/270,030, dated Nov. 16, 2011, seven pages.
U.S. Office Action, U.S. Appl. No. 12/270,348, dated Jun. 22, 2011, sixteen pages.
Wang, Y. et al., "A Novel Strategy to Engineer DNA Polymerases for Enhanced Processivity and Improved Performance in Vitro," *Nucleic Acids Res.*, 2004, pp. 1197-1207, vol. 32, No. 3.

(56) References Cited

OTHER PUBLICATIONS

Zhang, C. et al., "Miniaturized PCR chips for nucleic acid amplification and analysis: latest advances and future trends," *Nucleic Acids Research*, 2007, pp. 4223-4237, vol. 35, No. 13.
U.S. Office Action, U.S. Appl. No. 13/267,767, dated Apr. 24, 2015, 14 pages.
U.S. Office Action, U.S. Appl. No. 13/267,767, dated Nov. 6, 2014, 12 pages.

* cited by examiner

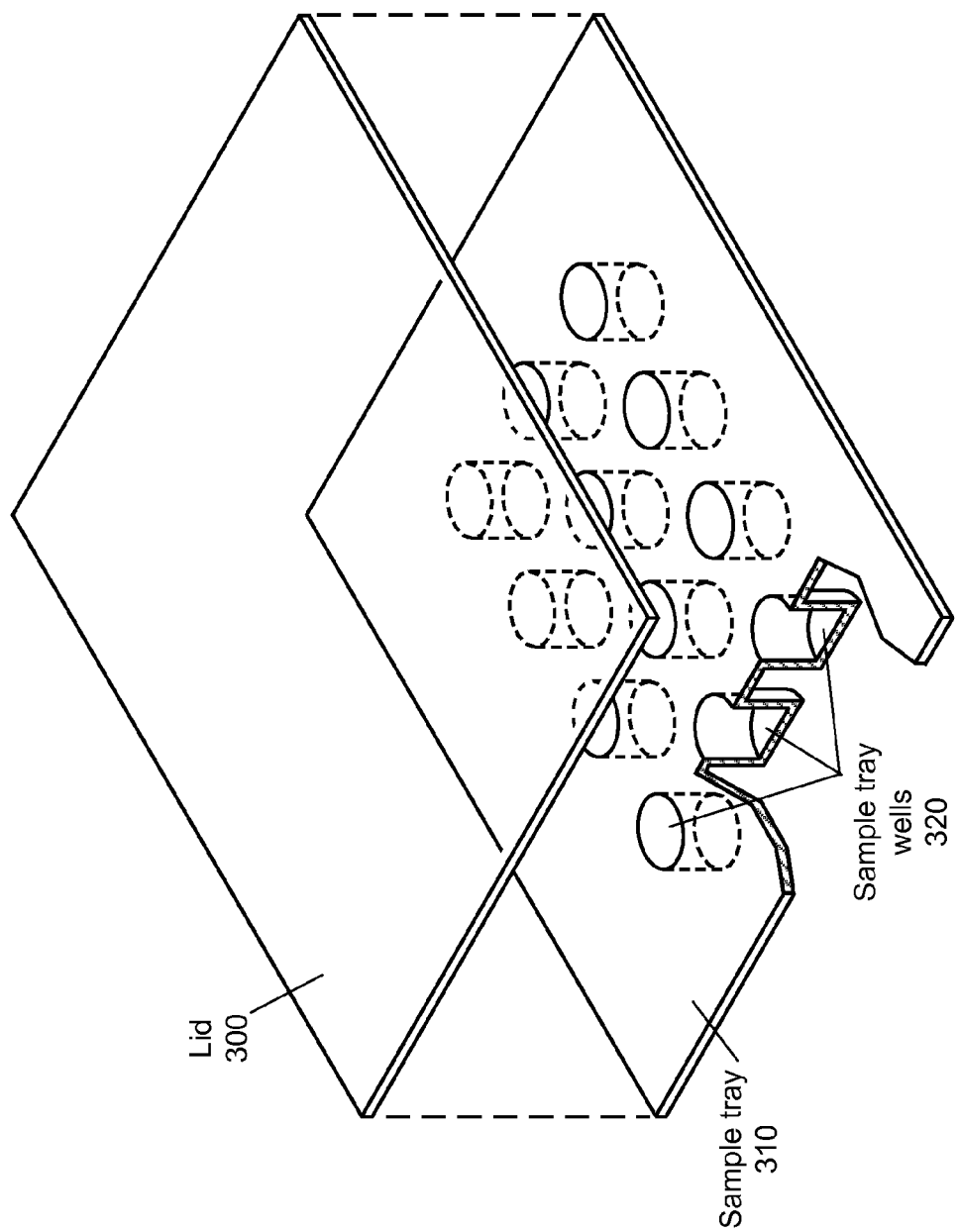

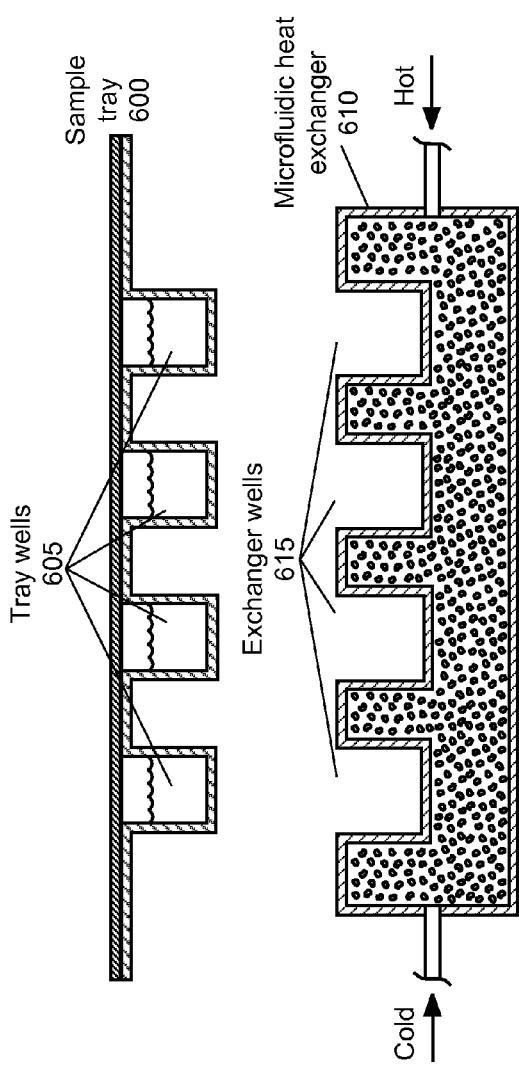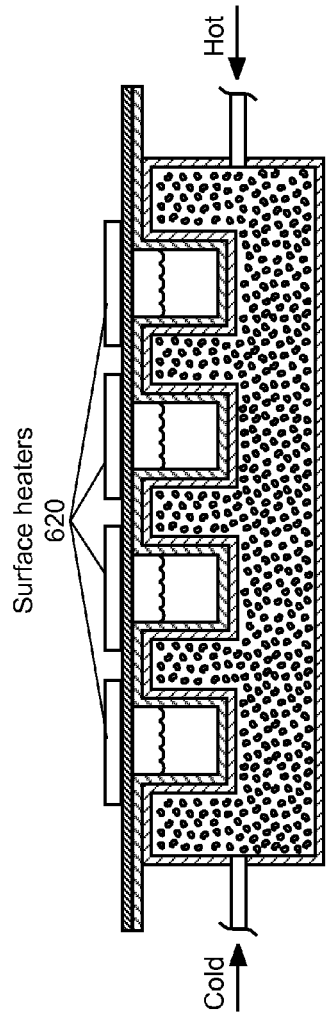

METHODS AND COMPOSITIONS FOR RAPID THERMAL CYCLING

RELATED APPLICATIONS

This application is a continuation of U.S. application Ser. No. 13/267,767, filed Oct. 6, 2011, now U.S. Pat. No. 9,170,028, which claims the benefit of U.S. Provisional Application No. 61/390,383, filed Oct. 6, 2010; U.S. Provisional Application No. 61/390,415, filed Oct. 6, 2010; U.S. Provisional Application No. 61/390,425, filed Oct. 6, 2010; U.S. Provisional Application No. 61/390,433, filed Oct. 6, 2010; U.S. Provisional Application No. 61/390,441, filed Oct. 6, 2010; U.S. Provisional Application No. 61/390,452, filed Oct. 6, 2010; and U.S. Provisional Application No. 61/512,393, filed Jul. 27, 2011, the content of each of which are incorporated by reference herein in its entirety.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

REFERENCE TO SEQUENCE LISTING

This application includes a Sequence Listing submitted electronically as a text file named 30582US_CRF_sequencelisting.TXT, created on Nov. 7, 2011, with a size of 2,413 bytes. The sequence listing is incorporated by reference.

FIELD OF THE INVENTION

The exemplary embodiments relate to thermal cycling and more particularly to a rapid microfluidic thermal cycler.

BACKGROUND OF THE INVENTION

PCR is the gold standard for fast and efficient nucleic acid analysis. It is the best method for genetic analysis, forensics, sequencing, and other critical applications because it is unsurpassed in specificity and sensitivity. By its very nature the method utilizes an exponential increase in signal, allowing detection of even single-copy nucleic acids in complex, real environments. Accordingly, PCR systems are ubiquitous, and the market for a faster thermocycling method is significant. Recent advancements in microfluidics allow the miniaturization and high throughput of on-chip processes, but they still lack the speed and thermal precision needed to revolutionize the field.

Robotic-based PCR systems are very slow in reaction speed, and utilize heating technologies with much less precision and accuracy. These systems typically couple auto-pipettes with robotic manipulators to measure, mix, and deliver sample and reagents. Accordingly, these systems are complex, expensive, and difficult to miniaturize.

SUMMARY OF THE INVENTION

An apparatus for thermally cycling a material is described. A microfluidic heat exchanger including one or more exchanger wells for receiving samples to be thermally cycled is coupled to a first tank and a second tank. The microfluidic heat exchanger includes an impermeable exterior and a porous medium interior. The first tank contains fluid at a first temperature, and the second tank contains fluid at a second temperature. A valve is coupled to the first tank and the second tank, and a pump is coupled to the valve. The valve allows a volume of fluid to flow from the pump through the valve and through the first tank and into the porous medium from a first direction when the valve is in a first position. The valve allows a volume of fluid to flow from the pump through the valve and the second tank into the porous medium from a second direction when the valve is in a second position.

In one embodiment, a reservoir tank is coupled to the valve and the pump. When the pump pumps a volume of fluid through the valve, the pump obtains the fluid from the reservoir tank. When the valve is in the first position, an equal volume of fluid flows from the second tank through the valve and into the reservoir tank. Likewise, when the valve is in the second position, an equal volume of fluid flows from the first tank through the valve and into the reservoir tank. In one embodiment, a first shunt valve is coupled between the first tank and the microfluidic heat exchanger, and a second shunt valve is coupled between the second tank and the microfluidic heat exchanger. The shunt valves are configured to direct fluid flow from the porous medium into the reservoir tanks. A controller may direct the switching of valve positions for the valve and the shunt valves based on the temperature of the samples.

In one embodiment, the microfluidic heat exchanger is configured to receive a sample tray. The sample tray may include one or more sample wells, and may be configured to align with the microfluidic heat exchanger such that the sample wells align with and are inserted into the microfluidic heat exchanger's wells when the sample tray is placed on the microfluidic heat exchanger. The microfluidic heat exchanger may include an electrical heater, such as a surface heater or an internal heater. The electrical heater may supplement the heating of samples by fluid flowing through the porous medium, or may replace the heating of samples by fluid flowing through the porous medium, obviating the need for a second tank.

The features and advantages described in the specification are not all inclusive and, in particular, many additional features and advantages will be apparent to one of ordinary skill in the art in view of the drawings and specification. Moreover, it should be noted that the language used in the specification has been principally selected for readability and instructional purposes, and may not have been selected to delineate or circumscribe the inventive subject matter.

BRIEF DESCRIPTION OF THE DRAWINGS

FIG. 3 illustrates a perspective view of a sealable sample tray and tray lid in accordance with one embodiment.

FIG. 6a illustrates a cutaway side view of a sealed sample tray above a microfluidic heat exchanger in accordance with one embodiment.

FIG. 6b illustrates a cutaway side view of a surface heaters placed upon a sealed sample tray, the sample tray placed upon a microfluidic heat exchanger in accordance with one embodiment.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Thermal Cycling System Overview

Figure 1:
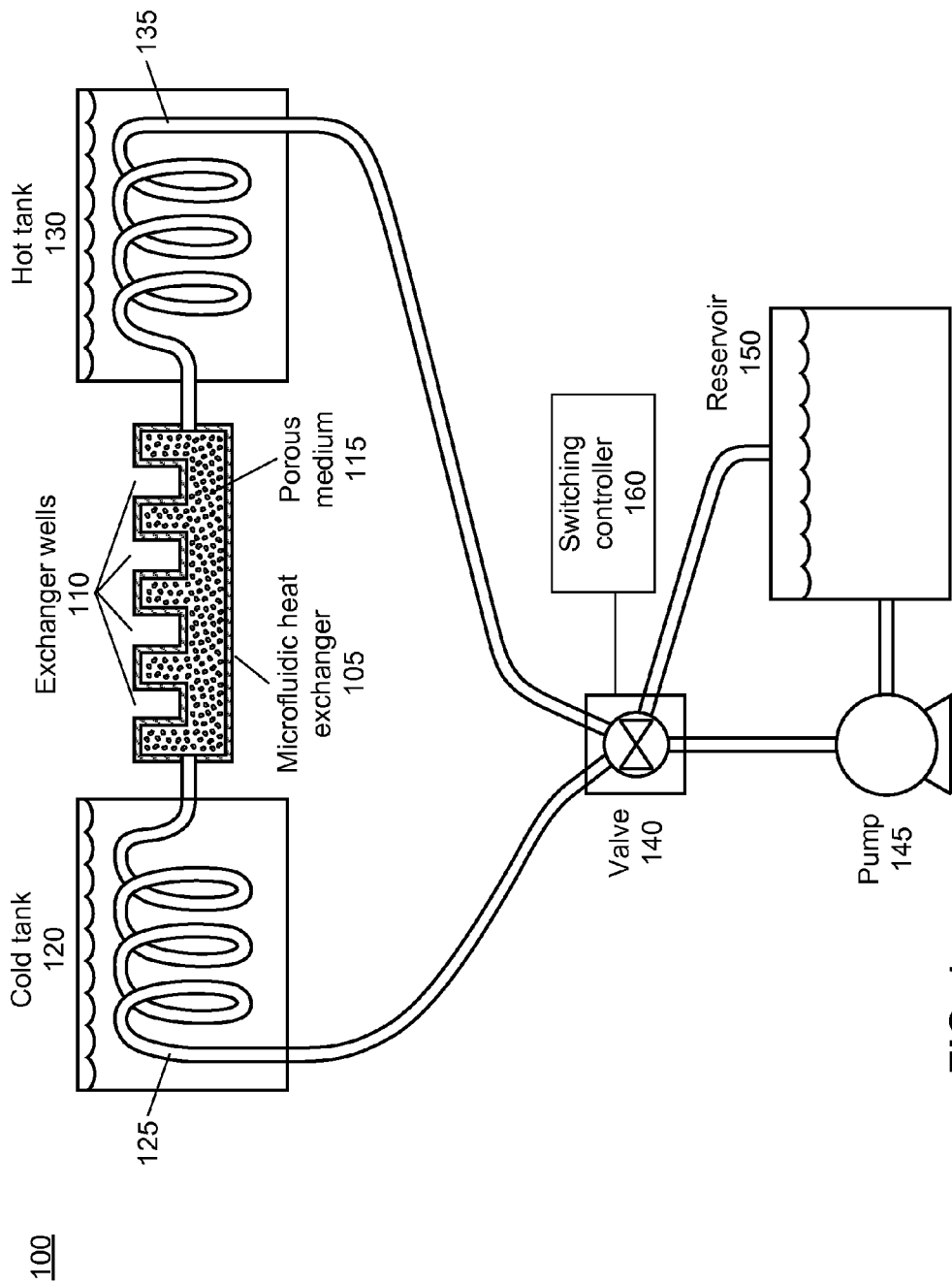
FIG. 1 illustrates a microfluidic heat exchanger in a thermal cycling system in accordance with one embodiment.

FIG. 1 illustrates a microfluidic heat exchanger in a thermal cycling system in accordance with one embodiment. Various embodiments of the thermal cycling system 100 will be described as polymerase chain reaction (PCR) system, however it is to be understood that the system 100 can be used for other thermal cycling systems.

The system 100 of FIG. 1 includes a microfluidic heat exchanger 105, a cold tank 120, a hot tank 130, a valve 140, a pump 145, a reservoir 150, and a switching controller 160. Although the embodiment of FIG. 1 contains a cold tank 120 and a hot tank 130, it should be noted that the tanks may contain fluid at any temperature, and that the terms "cold" and "hot" are used for descriptive purposes only, and are not intended to be limiting in any way. For example, both tanks may contain cold fluid or hot fluid. Further, in alternative embodiments, the system of FIG. 1 may include fewer, additional, or different components.

The microfluidic heat exchanger 105 includes one or more exchanger wells 110. The microfluidic heat exchanger 105 also includes a porous medium 115. The microfluidic heat exchanger 105 is configured to receive one or more samples to be thermally cycled in the exchanger wells 110, and to cycle the received samples between two or more temperatures by flowing fluids at the two or more temperatures through the porous medium 115.

In one embodiment, the exterior of the microfluidic heat exchanger 105 includes a solid, impermeable surface surrounding the porous medium 115. In this embodiment, the impermeable surface may make up the walls and the bottom of the exchanger wells 110. In order to maximize the heat exchange between fluid within the porous medium 115 and the samples placed in the exchanger wells 110, the impermeable surface of the microfluidic heat exchanger 105 may include a highly thermally conductive material, including but not limited to, copper, aluminum, gold-plated metallics, silicon, iron, and steel.

The microfluidic heat exchanger 105 includes two or more inlet channels through the surface of the microfluidic heat exchanger 105. In one embodiment, the two or more inlet channels are the only openings within the surface of the microfluidic heat exchanger 105. The inlet channels are configured to allow fluid to flow from a source external to the microfluidic heat exchanger 105 into the porous medium 115 and vice versa. In one embodiment, fluid pumped into the porous medium 115 through an inlet channel flows through the porous medium 115 and out of the remaining inlet channels. For the remainder of this description, the microfluidic heat exchanger 105 is described as having two inlet channels for the purposes of simplicity, but alternative embodiments of the system 100 described herein are implemented with a microfluidic heat exchanger 105 with any number of inlet channels.

In one embodiment, the porous medium 115 may completely fill the interior cavity of the microfluidic heat exchanger 105 formed by the solid, impermeable exterior of the microfluidic heat exchanger 105. The porous medium 115 of the microfluidic heat exchanger 105 may include any material which allows fluid to flow through the medium, for instance a hardened foam. The porous medium 115 may be of uniform porosity and permeability. Alternatively, the porous medium 115 may be of a gradient porosity. In one embodiment, the permeability and the porosity of the porous medium 115 are $3.74 \times 10^{-10}$ m$^2$ and 0.45, respectively. In one embodiment, the porosity of the porous medium 115 is between 0.2 to 0.7. The density of the porous medium 115 may be between 10% and 30%.

In order to maximize heat exchange, the porous medium 115 may be composed of a highly thermally conductive material. For example, the porous medium 115 may be composed of copper foam, gold or gold-deposited foam, any metallic or otherwise thermally-conductive foam, metallic composites with isotropic or anisotropic properties, micro-machined or photolithographically-produced microchannel inserts, and doped ceramics. The structure of the porous medium 115 may also include pillars extending from the top, bottom and sides of the porous medium 115, in either a structured order or randomly. The properties (such as the conduction rates and gradients) of the porous medium 115 may be selected for homogenous heat transfer across the heat exchanger. In one embodiment, the porous medium 115 may be produced by 3-dimensional printing technologies.

The microfluidic heat exchanger 105 may include any number and arrangement of the exchanger wells 110, and the exchanger wells 110 may be of any size or shape. In one embodiment, the exchanger wells 110 are configured to directly receive and contain samples to be thermally cycled. Alternatively, the exchanger wells 110 may be configured to receive a sample tray containing samples to be thermally cycled. In such an embodiment, the exchanger wells 110 may be arranged to receive a similarly arranged sample tray such that the wells of the sample tray fit into the exchanger wells 110. Such an embodiment will be discussed in greater detail in FIGS. 3-6. The size and geometry of the exchanger wells 110 may be designed in order to accommodate the diffusion time requirements of PCR. For example, the surface area of the exchanger wells 110 may be maximized relative to the volume of the exchanger wells 110, subject to the feasibility of manufacturing constraints. In one embodiment, the exchanger wells 110 are configured to receive and contain samples of 1-10 µL, 3-7 µL or approximately 5 µL. It is not strictly necessary for all wells to be configured identically, provided that they accommodate a sample holder, if used with a sample holder.

As discussed above, the thermal cycling system 100 contains a cold tank 120 and a hot tank 130. The cold tank 120 contains a fluid at a first temperature T1, and the hot tank 130 contains a fluid at a second temperature T2. As also discussed above, the tanks may contain fluids at any temperature, but for the purposes of simplicity, the remainder of this discussion will assume that the temperature T2 is a higher temperature than the temperature T1. The fluid contained within the cold tank 120 and the hot tank 130 may be any fluid, for instance water. The tanks may be configured to maintain the temperatures T1 and T2 of the fluids contained with the tank to within a certain variance or temperature interval. In order to maintain the temperatures T1 and T2, the tanks may be insulated, and may contain heaters or coolers to increase or decrease the temperatures of the fluids within the tanks.

In one embodiment, the cold tank 120 contains tubing 125 and the hot tank 130 contains tubing 135. The tubing 125 and 135 may be coiled as illustrated in FIG. 1, and may be coupled to the microfluidic heat exchanger 105 at the two inlet channels of the microfluidic heat exchanger 105. In such a configuration, fluid may flow from the tubing 125 in a first direction through the porous medium 115 into the tubing 135, and from the tubing 135 in a second direction through the porous medium 115 into the tubing 125. As used herein, the first direction refers to fluid flowing from a first inlet channel through the porous medium 115 and out of a second inlet channel, and the second direction refers to fluid flowing from the second inlet channel through the porous medium 115 and out of the first inlet channel. The two inlet channels may be located on opposite ends of the microfluidic heat exchanger 105, and the exchanger wells 110 may be located directly between the two inlet channels, such that the opportunity for heat exchange between flowing fluid and the walls of the exchanger wells 110 is maximized for fluid flowing from the tubing 125 through the porous medium 115 to the tubing 135 and vice versa. As used herein, "tubing" refers to any connecting material capable of securely containing flowing fluid, such as pipes, ducts, tubes or any other material.

In one embodiment, the tubing 125 and 135 contain a fluid separate from the fluid contained within the cold tank 120 and the hot tank 130. In this embodiment, heat transfer from the fluid within the tanks 120 and 130 to the fluid within the tubing 125 and 135 adjusts the temperature of the fluid within the tubing 120 and 130 to the temperature T1 and T2 of the cold tank 120 and the hot tank 130, respectively. This allows fluid at temperatures T1 and T2 to flow from the tubing 125 and 135, respectively, into the porous medium 115. In such an embodiment, the tubing 125 and 135 is composed of a material conducive to heat transfer, such as a highly thermally conductive material.

In an alternative embodiment, in place of the tubing 125 and 135, fluid from the cold tank 120 and the hot tank 130 flows directly into the porous medium 115. In this embodiment, the cold tank 120 and the hot tank 130 may be coupled to the inlet channels of the microfluidic heat exchanger 105 with tubing, but without the use of tubing within the tanks 120 and 130.

As illustrated in FIG. 1, the valve 140 is coupled to the cold tank 120, the hot tank 130, the pump 145, and the reservoir 150. The valve may be any type of valve configured to couple the pump 145 to one of the cold tank 120 and the hot tank 130 and to couple the reservoir 150 to the other of the cold tank 120 and the hot tank 130 when the valve 140 is in a first position, and to switch the tanks (120 or 130) coupled to the pump 145 and the reservoir 150 when the valve 140 is in a second position. For example, if the valve 140 is in the first position, the pump 145 is coupled to the cold tank 120 and the reservoir 150 is coupled to the hot tank 130. In this example, if the valve 140 is in the second position, the pump 145 is coupled to the hot tank 130 and the reservoir 150 is coupled to the cold tank 120. The valve 140 may be coupled to the tanks 120 and 130, and the pump 145 and reservoir 150 by any means such that fluid may flow between the tanks 120 and 130 and the pump 145 and the reservoir 150 through the valve 140. For example, the valve 140 may be coupled to the tanks 120 and 130 and the pump 145 and the reservoir 150 with tubing.

The pump 145 as mentioned above is coupled to the valve 140, and is also coupled to the reservoir 150. The reservoir 150 contains fluid, and may be of any size and or configuration. In one embodiment, the pump 145 is configured to pump fluid from the reservoir 150 through the valve 140 to one of the tanks 120 or 130. In an alternative embodiment, the pump 145 is configured to pump fluid from one of the tanks 120 or 130 through the valve 140 and into the reservoir 150.

In one embodiment, the system 100 is a closed system. Thus, for a volume of fluid pumped from the reservoir 150 by the pump 145 through the valve 140 into (for example) the cold tank 120, an equal volume of fluid flows from the cold tank 120 to the porous medium 115, from the porous medium 115 to the hot tank 130, and from the hot tank 140 through the valve 140 and into the reservoir 150. Thus, for any volume of fluid pumped by the pump 145 through the microfluidic heat exchanger 105, an equal volume of fluid flows through the microfluidic heat exchanger 105 into the reservoir 150.

When the valve 140 is in the first valve position, the fluid pumped by the pump 145 flows through the microfluidic heat exchanger 105 in a first direction (for instance, from the cold tank 120 through the microfluidic heat exchanger 105 into the hot tank 130). When the valve 140 is in the second valve position, the fluid pumped by the pump 145 flows through the microfluidic heat exchanger 105 in a second direction (for instance, from the hot tank 130 through the microfluidic heat exchanger 105 into the cold tank 120).

In one embodiment, the pump 145 continuously pumps fluid from the reservoir 150 through the valve 140 into the microfluidic heat exchanger 105, and the valve 140 iteratively switches between the first valve position and the second valve position, causing the direction in which fluid is flowing through the porous medium 115 to iteratively switch direction. When fluid is flowing through the porous medium 115 in a first direction, for instance from the cold tank 120 to the hot tank 130, the temperature of the fluid flowing through the porous medium 115 is the temperature of the fluid within the cold tank 120, for instance T1. When fluid is flowing through the porous medium 115 in a second direction, for instance from the hot tank 130 to the cold tank 120, the temperature of the fluid flowing through the porous medium 115 is the temperature of the fluid within the hot tank 130, for instance T2. Thus, the iterative switching of directions in which fluid is flowing through the porous medium 115 results in the iterative switching of the temperature of the fluid flowing through the porous medium 115 between T1 and T2. As a result, the iterative switching of the temperature of the fluid flowing through the porous medium 115 causes the temperature of the surfaces of the exchanger wells 110 to iteratively switch between T1 and T2.

When a volume of fluid at temperature T1 flows from the cold tank 120 through the porous medium 115 to the hot tank 130, the temperature of the fluid in the hot tank 130 causes the temperature of the volume of fluid from the cold tank 120 to adjust to T2. While the adjustment of temperature of the volume of fluid from the cold tank 120 is not instantaneous, particularly in the instance where fluid flows into the tubing 135 within the hot tank 130, the volume of the fluid in the hot tank 130 may be large enough relative to the volume of fluid from the cold tank 120 such that the adjustment of temperature of the volume of fluid from the cold tank 120 from T1 to T2 is sufficiently fast. Likewise, the volume of the cold tank 120 may be large enough relative to a volume of fluid which flows from the hot tank 130 to the cold tank 120 such that the adjustment of temperature of the volume of fluid from the hot tank 130 from T2 to T1 is sufficiently fast. In order to further aid the adjustment of temperature of fluid which flows into the tanks 120 and 130, heaters and coolers may be used to adjust the temperature of fluid more rapidly.

Figure 2:
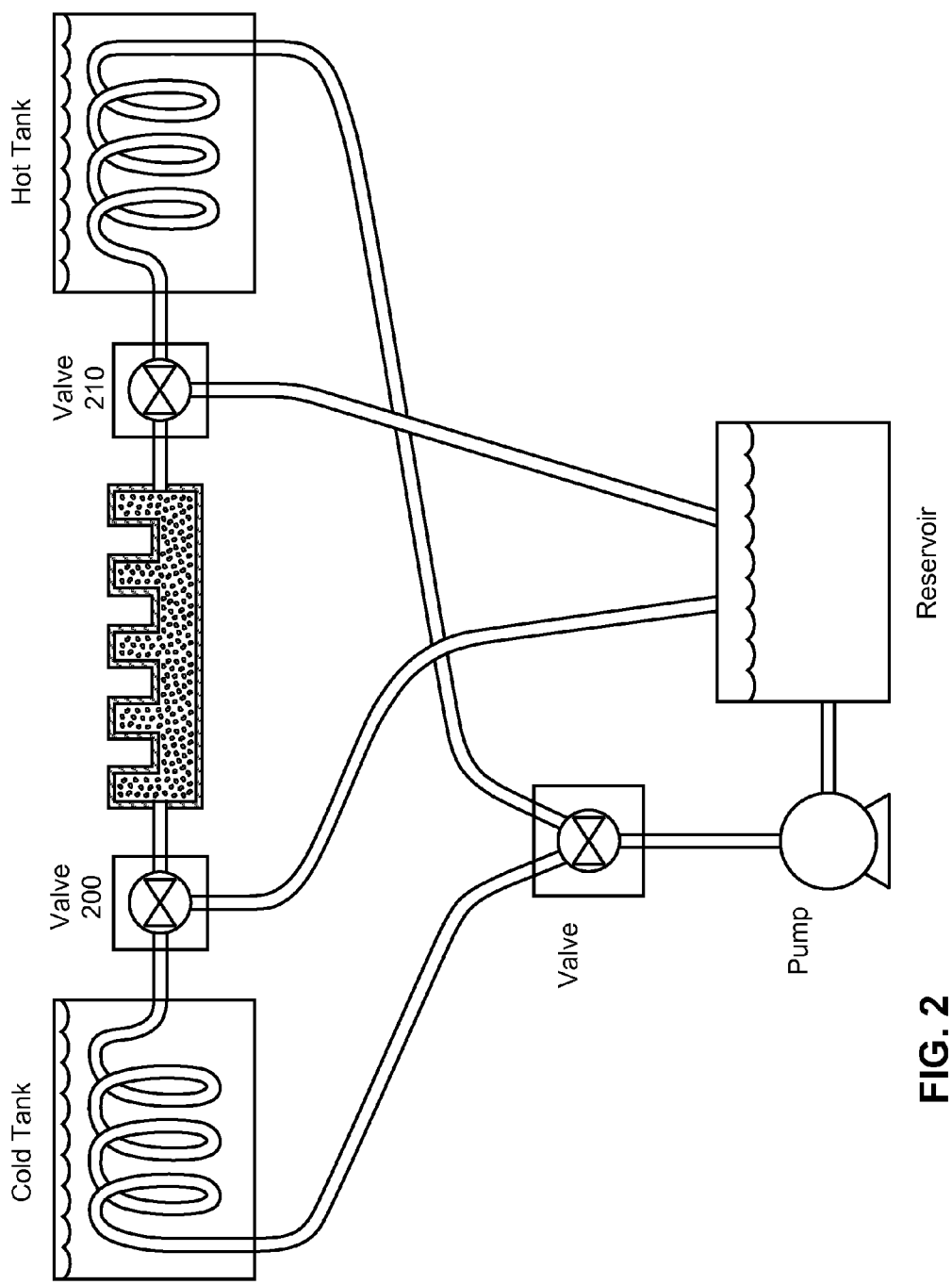
FIG. 2 illustrates a microfluidic heat exchanger in a thermal cycling system with reservoir shunt valves in accordance with one embodiment.

In order to completely eliminate the need to adjust the temperature of fluids which flow between tanks 120 and 130 through the porous medium 115, shunt valves may be used which divert fluid flowing through the porous medium 115 directly into the reservoir 150. FIG. 2 illustrates a microfluidic heat exchanger in a thermal cycling system with reservoir shunt valves in accordance with one embodiment. In the embodiment of FIG. 2, a first shunt valve (valve 200) is coupled between the cold tank 120 and the microfluidic heat exchanger 105, and a second shunt valve (valve 210) is couple between the hot tank 130 and the microfluidic heat exchanger 105. Valves 200 and 210 are also coupled directly to the reservoir 150. As discussed above, the valves 200 and 210 may be coupled to the tanks 120 and 130, the microfluidic heat exchanger 105, and the reservoir 150 with tubing.

The shunt valves 200 and 210 are configured such that when the pump 145 is pumping a volume of fluid through the valve 140 to the cold tank 120, the valve 200 is in a first valve position which allows an equal volume of fluid to flow from the cold tank 120 through the valve 200 to the microfluidic heat exchanger 105, and the valve 210 is in a second valve position which allows an equal volume of fluid to flow from the microfluidic heat exchanger 105 through the valve 210 into the reservoir 150. Likewise, when the pump 145 is pumping a volume of fluid through the valve 140 to the hot tank 130, the valve 210 is in a first valve position which allows an equal volume of fluid to flow from the hot tank 130 through the valve 210 to the microfluidic heat exchanger 105, and the valve 200 is in a second valve position which allows an equal volume of fluid to flow from the microfluidic heat exchanger 105 through the valve 200 to the reservoir 150.

In the embodiment of FIG. 2, the valves 200 and 210 may be configured to switch valve positions in response to a switch in valve position by the valve 140. For example, if the valve 140 switches from the second valve position to the first valve position, the valve 200 switches to the first valve position, and the valve 210 switches to the second valve position. If the valve 140 switches from the first valve position to the second valve position, the valve 200 switches to the second valve position, and the valve 210 switches to the first valve position. In such an embodiment, fluid at a first temperature never flows directly into a tank containing fluid at a second temperature from the porous medium 115. This allows the tanks 120 and 130 to be able to provide fluid of temperatures T1 and T2, respectively, to the microfluidic heat exchanger 105 more quickly without the extra time and energy involved in immediately adjusting the fluid pumped into the tanks 120 and 130 from the microfluidic heat exchanger 105.

Thermal Cycling System Switching Controller

The thermal cycling system 100 may include a switching controller 160 for controlling the operation of valves 140, 200, and 210 and the pump 145. The switching controller 160 may be coupled to one or more temperature sensors configured to determine the temperature of samples in the exchanger wells 110, the temperature of the surface of the exchanger wells 110, the temperature of the porous medium 115, the temperature of the fluid in the porous medium, or the temperature of any other suitable component of the system 100. The switching controller 160 may cause the pump 145 to begin pumping fluid into the microfluidic heat exchanger 105 in response to a user initiating a thermal cycling operation, and may cause the pump 145 to stop pumping fluid into the microfluidic heat exchanger 105 in response to a determination to end a thermal cycling operation, based on, for example, user input, the passage of a pre-determined threshold of time, the cycling of a pre-determined number of cycles, and the like. For simplicity, the remainder of this description will be limited to the arrangement where the switching controller 160 is operating based on the determined temperature of the samples, though other embodiments may operate based on the determined temperature of the surface of the exchanger wells 110, the temperature of the porous medium 115, etc.

The switching controller 160 may determine (via one or more temperature sensors) that the temperature of samples in the exchanger wells 110 falls below a first threshold (T3) when fluid from the cold tank 120 is flowing through the porous medium 115. In response to such a determination, the switching controller 160 may switch the configuration of the valve 140, causing the valve 140 to go from a first position to a second position, and switching the direction of fluid flowing through the porous medium 115 so that fluid flows into the porous medium 115 from the hot tank 130. Likewise, if the switching controller 160 determines that the temperature of samples in the exchanger wells 110 exceeds a second threshold (T4) when fluid from the hot tank 130 is flowing through the porous medium 115, the switching controller 160 may switch the configuration of the valve 140, causing the valve 140 to go from a second position to a first position, and switching the direction of fluid flowing through the porous medium 115 so that fluid flows into the porous medium 115 from the cold tank 120. The switching controller 160 may also control the valves 200 and 210, causing the valves 200 and 210 to switch positions when the valve 140 switches positions.

The first and second switching controller temperature thresholds T3 and T4 may be pre-determined. In one embodiment, T3 and T4 are determined to be within a pre-determined number of degrees (for instance, degrees Kelvin) of T1 and T2. Alternatively, T3 and T4 may be determined based on the requirements of the PCR reaction or on the samples to be thermally cycled, and the temperatures T1 and T2 of the tanks 120 and 130, respectively, may be determined based on T3 and T4. Generally, T3 represents a temperature greater than the temperature represented by T1, and T4 represents a temperature less than the temperature represented by T2. In one example embodiment, T1 is approximately 51° C., T2 is approximately 98° C., T3 is approximately 62° C., and T4 is approximately 90° C.

It should be noted that even after the switching controller 160 causes the direction of fluid flowing through the porous medium 115 to switch, the temperature of the samples may continue to rise and fall past the thresholds T3 and T4. For example, if the switching controller 160 causes fluid flowing through the porous medium 115 from the cold tank 120 to switch directions such that the fluid flowing through the porous medium 115 flows from the hot tank 130, the temperature of the samples in the exchanger wells 110 may continue to fall for some period of time before the temperature of the samples rises due to the increase in temperature from the fluid at temperature T2. Likewise, if the switching controller 160 causes fluid flowing through the porous medium 115 from the hot tank 130 to switch directions such that the fluid flowing through the porous medium 115 flows from the cold tank 120, the temperature of the samples in the exchanger wells 110 may continue to rise for some period of time.

Such a delay in the switching between the rise and fall of the temperature of the samples in the exchanger wells 110 may be due to delays in switching the position of the valve 140, delays in the flow of fluids from the tanks 120 and 130 into the porous medium 115, or natural physical delays in heat exchange from the fluids flowing through the porous medium 115 to the samples in the exchanger wells 110. In one embodiment, delays in the switching between the rise and fall of the temperature of the samples in the exchanger wells 110 may be planned for in advance. For example, if samples to be thermally cycled are to be cycled between some temperature T5 such that T1<T5<T3 and some temperature T6 such that T2>T6>T4, a designer of the system 100 may determine (1) the extent to which the temperatures of the samples may fall after switching between fluid at temperature T1 flowing through the porous medium 115 to fluid at temperature T2 flowing through the porous medium 115; and (2) the extent to which the temperatures of the samples may rise after switching between fluid at temperature T2 flowing through the porous medium 115 to fluid at temperature T1 flowing through the porous medium 115, and may set the threshold temperatures T3 and T4 accordingly. This configuration beneficially allows a designer to prevent temperature overshoot, which might result in damage to the samples. In one example embodiment, T5 is approximately 54° C., and T6 is approximately 94° C.

In one embodiment, the microfluidic heat exchanger utilizes bias heating to maintain the solid state heat exchanger 400 at a bias temperature. For example, the microfluidic heat exchanger may utilize a bias temperature of 50° C. In one embodiment, the microfluidic heat exchanger utilizes bias cooling. For example, the microfluidic heat exchanger may utilize a heat sink with a speed-controllable fan to implement bias cooling. In one embodiment, the parameters of the bias heating and bias cooling are dependent on the requirements of PCR. The bias heating and bias cooling may be implemented using the fluids in the cold tank 120 and hot tank 130 described herein, or using internal or surface heaters as described below.

In one embodiment, the switching controller 160 may determine T3 and T4 in real-time. For example, the switching controller 160 may determine that, in response to causing the valve 140 to switch positions when the samples in the exchanger wells 110 reach T3, the temperature of the samples does not quite reach T5. In this instance, the switching controller 160 may decrease T3 for subsequent cycles. Likewise, the switching controller 160 may increase T4 in response to a determination that the temperature of the samples does not quite reach T6. In one embodiment, the switching controller 160 utilizes proportional error calculations to determine temperature switching thresholds. In one embodiment, the switching controller 160 utilizes proportional integral derivative (PID) control schemes to accommodate higher fluid temperatures or tighter temperature tolerances.

The switching controller 160 may store successful threshold values (the temperature thresholds T3 and T4 that produce the desired sample temperatures T5 and T6 with an acceptable margin of error, respectively) in a parameters database. Further, the switching controller 160 may store the time intervals between switching the position of the valve 140 for one or more experiments, the number of cycles performed, the temperatures of fluid in the cold tank 120 and the hot tank 130, the temperature of fluid in the reservoir 150, or any other relevant parameters (such as parameters related to the application of surface heaters or other heaters discussed below). The stored thresholds, temperatures and other parameters (referred to herein collectively as the "experiment parameters") may be stored in conjunction with the experiment type and the sample type associated with the stored parameters. When a new experiment is being performed by the thermal cycling system 100, the switching controller 160 may query the parameters database to retrieve parameters for previously performed experiments similar to the new experiment.

In one embodiment, the switching controller 160 causes the valve 140 to switch positions after the passage of a pre-determined amount of time, independently of the temperature of the samples in the exchanger wells 110. For example, the switching controller 160 may cause the valve 140 to switch positions approximately every 1.5 seconds. Alternatively, the switching controller 160 may cause the valve 140 to switch positions after the switching controller 160 first detects that the temperature of samples in the exchanger wells 110 has exceeded or fallen below a particular threshold and then after a pre-determined amount of time has passed. In this embodiment, the samples are held above or below the particular threshold for a guaranteed amount of time before the direction of fluid flowing through the porous medium 115 is switched.

Figure 8:
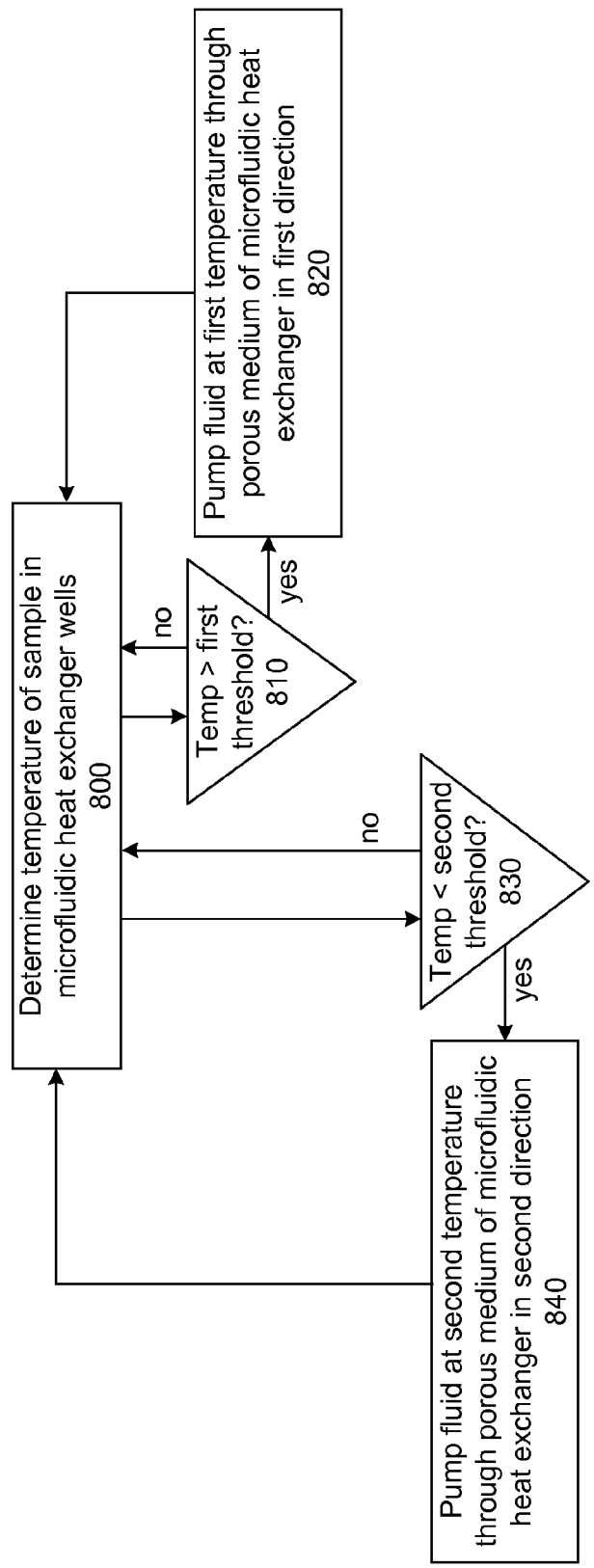
FIG. 8 is a flowchart illustrating the thermal cycling of a sample in a microfluidic heat exchanger in accordance with one embodiment.

FIG. 8 is a flowchart illustrating the thermal cycling of a sample in a microfluidic heat exchanger in accordance with one embodiment. The temperature of a sample in one or more microfluidic heat exchanger wells is determined 800. As discussed above, instead of determining the temperature of the sample itself, the temperature of the walls of the exchanger wells or the temperature of the porous medium in the microfluidic heat exchanger may be determined and used for the purpose of thermal cycling temperature thresholds. If the determined temperature exceeds 810 a first threshold, fluid at a first temperature is pumped 820 through the porous medium of the microfluidic heat exchanger in a first direction. If the determined temperature falls below 830 a second threshold, fluid at a second temperature is pumped 840 through the porous medium of the microfluidic heat exchanger in a second direction. This process may repeat for a set number of iterations, or for a set amount of time.

Thermal Cycling System Sample Tray

FIG. 3 illustrates a perspective view of a sealable sample tray and tray lid in accordance with one embodiment. The sealable sample tray is configured to allow a user to load samples to be thermally cycled into the sealable sample tray, and to allow a user to thermally cycle the samples loaded into the sample with the thermal cycling system 100.

The embodiment of FIG. 3 includes a lid 300 and a sample tray 310. The lid 300 and sample tray 300 may be made of any material, for instance a polymer film (such as polypropylene), aluminum, copper, silicon, or any other suitable material. In one embodiment, the lid 300 and sample tray 310 are made of a highly thermally conductive material to aid in thermal cycling. Alternatively, the lid 300 and sample tray 310 may be made of a poorly thermally conductive material, but may be made extremely thin such that the heat exchange distance is minimized to compensate for the poor conductivity of the material. The lid 300 and the sample tray 310 may be made of an optically transparent material such that the fluorescence of samples can be monitored throughout the thermal cycling process, providing a user with the ability to conduct real-time assays with samples.

In one embodiment, the sample tray 310 includes sample tray wells 320 for inserting and containing samples to be thermally cycled. The sample tray wells 320 may be of any size, shape or configuration, and although 12 wells are displayed in the embodiment of FIG. 3, the sample tray 310 may contain any number of sample tray wells 320. In one embodiment, the size, shape, configuration and number of sample tray wells 320 are configured based on the size, shape, configuration and number of exchanger wells 110, such that the sample tray 310, when placed upon the microfluidic heat exchanger 105, results in the sample tray wells 320 aligning with the exchanger wells 110. In such an embodiment, the contact between the outer surface of the sample tray wells 320 and the inner surface of the exchanger wells 110 is maximized, aiding the thermal cycling of samples to be thermally cycled.

The shape of the sample tray wells 320 may be hemispherical, such that the distance of thermal diffusion into or out of the wells is constant from all sides of the wells to the center of the sample contained within the wells. The shape of the sample tray wells 320 may be conical, such that the surfaces of the wells are more rigid and less likely to deform during thermal cycling. The shape of the sample tray wells 320 may be cylindrical, such that the largest sample volume for a constant cross-sectional area may be thermally cycled. The shape of the sample tray wells 320 may also be a morphology of hemispherical, conical, cylindrical, and/or any other geometric configuration.

The lid 300 is configured to attach or seal to the sample tray 310. The lid 300 may be configured to seal each individual sample tray well 320 such that the sample tray well 320, when sealed, is air tight. In one embodiment, the lid 300 and the sample tray 310 seal using an adhesive liner on the lid 300 or the sample tray 310. The adhesive liner may be configured in any arrangement on the lid 300 or the sample tray 310. In one embodiment, adhesive liner is applied around the top edge of each sample tray well 320, sealing each sample tray well 320 individually when the lid 300 is sealed to the sample tray 310. The lid 300 may include a removable adhesive backing which protects an adhesive liner on the lid 300 until the removable adhesive backing is removed. In this embodiment, in order to apply and seal the lid 300 to the sample tray 310, a user must remove the removable adhesive backing such that the adhesive liner of the lid 300 is exposed, and place the lid 300 on the sample tray 310 such that the adhesive liner of the lid 300 adheres to the sample tray 310.

In one embodiment, the lid 300 and the sample tray 310 are resealable, allowing for multiple uses using the sample lid 300 and sample tray 310. Alternatively, the lid 300 and the sample tray 310 may be sealable only once, resulting in a disposable sample tray 310. In one embodiment, channels may be etched into the sample tray 310. In this embodiment, after the lid 300 is sealed to the sample tray 310, a vacuum may be applied to the channels to remove the air from within each sealed sample tray well 320.

In one embodiment, the sample tray wells 320 are pre-filled with reagents, e.g., reagents for a PCR reaction, and the lid 300 is pre-sealed to the sample tray 310 in order to prevent the reagents within the sample tray wells 320 from leaking. In such an embodiment, a user may remove the lid 300, may insert one or more samples to be thermally cycled into the reagents in the sample tray wells 320, and may re-seal the lid 300 onto the sample tray 310.

Once a thermal cycling process is complete, a user may remove the sample tray 310 from the microfluidic heat exchanger 105 so that the thermally cycled samples may be analyzed. In one embodiment, the thermally cycled samples may be analyzed by removing the lid 300 from the sample tray 310, and extracting the samples from the sample tray wells 320. Alternatively, the thermally cycled samples may be extracted by piercing the lid 300 using, for example, a hypodermic needle, and removing the thermally cycled samples with the hypodermic needle.

Figure 4A:
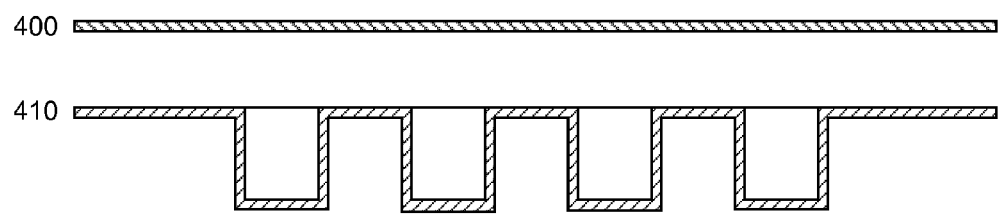
FIG. 4a illustrates a cutaway side view of an unsealed sample tray and tray lid in accordance with one embodiment.
Figure 4B:
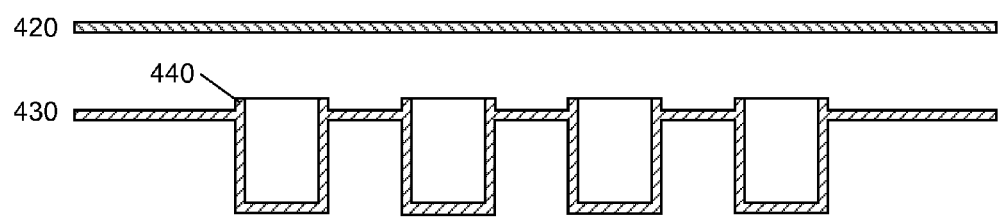
FIG. 4b illustrates a cutaway side view of an unsealed sample tray with protruding sample well ridges and tray lid in accordance with one embodiment.
Figure 4C:
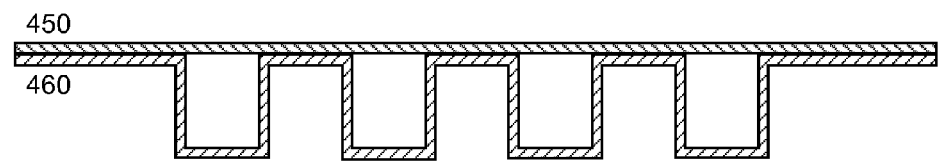
FIG. 4c illustrates a cutaway side view of a sealed sample tray and tray lid in accordance with one embodiment.

FIG. 4a illustrates a cutaway side view of an unsealed sample tray and tray lid in accordance with one embodiment. In this embodiment, the lid 400 is not sealed to the sample tray 410. FIG. 4b illustrates a cutaway side view of an unsealed sample tray with protruding sample well ridges and tray lid in accordance with one embodiment. In this embodiment, the lid 420 is not sealed to the sample tray 430. The sample tray 430 contains ridges 440 around the top edge of each sample well. The ridges beneficially help form a seal with the lid 420 when the lid 420 is sealed to the sample tray 430. FIG. 4c illustrates a cutaway side view of a sealed sample tray and tray lid in accordance with one embodiment. In this embodiment, the lid 450 is sealed to the sample tray 460 using, for example, an adhesive sealant.

Figure 5:
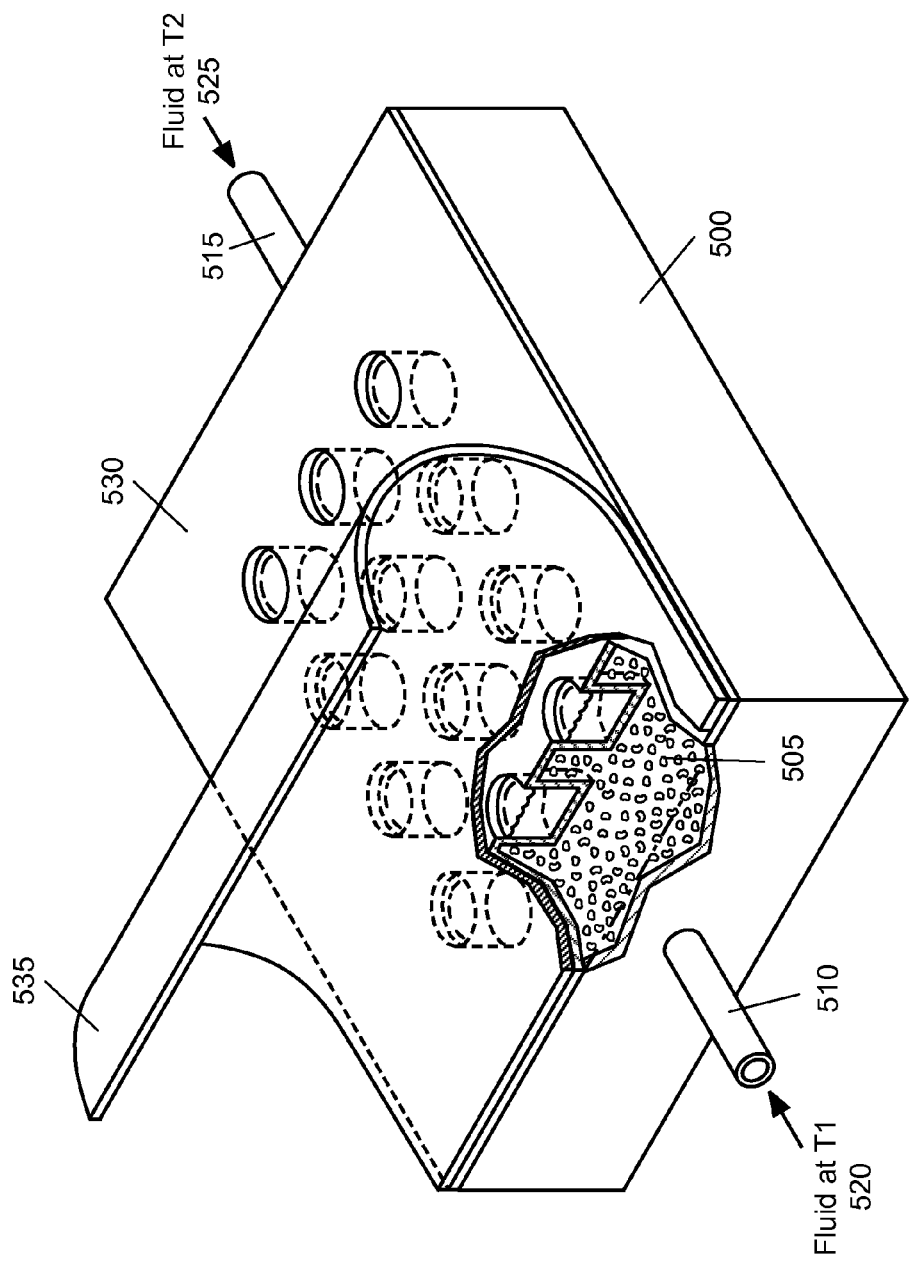
FIG. 5 illustrates a prospective view of a partially sealed sample tray and tray lid placed upon a microfluidic heat exchanger in accordance with one embodiment.

FIG. 5 illustrates a prospective view of a partially sealed sample tray and tray lid placed upon a microfluidic heat exchanger in accordance with one embodiment. In this embodiment, the microfluidic heat exchanger 500 includes a porous medium 505 interior, and a solid, impermeable exterior. Further, the microfluidic heat exchanger 500 includes an inlet channel 510 for receiving fluid of a temperature T1 510, and an inlet channel 515 for receiving fluid of a temperature T2 525. As discussed above, the inlet channels 510 and 515 are also configured to allow fluid within the porous medium 505 to flow out of the inlet channels 510 and 515.

In the embodiment of FIG. 5, the sample tray 530 is placed upon the microfluidic heat exchanger 500. In this embodiment, the sample wells of the sample tray 530 are configured to align with the exchanger wells, allowing the sample tray wells to be inserted into the exchanger wells when the sample tray 530 is aligned with the microfluidic heat exchanger 500. In the embodiment of FIG. 5, the sample tray lid 535 is partially sealed to the sample tray 530. In this embodiment, the sample tray lid 535 is made of a flexible material which allows the sample tray lid 535 to be rolled onto the sample tray 530 and sealed.

FIG. 6a illustrates a cutaway side view of a sealed sample tray above a microfluidic heat exchanger in accordance with one embodiment. In the embodiment of FIG. 6a, the sample tray lid is sealed to the sample tray 600, and the sample tray wells 605 contain samples to be thermally cycled. In this embodiment, the sample tray 600 has not been placed upon the microfluidic heat exchanger 610, which includes exchanger wells 615 which align with the sample tray wells 605. FIG. 6b illustrates a cutaway side view of a surface heaters placed upon a sealed sample tray, the sample tray placed upon a microfluidic heat exchanger in accordance with one embodiment. In the embodiment of FIG. 6b, the sample tray 600 has been placed upon the microfluidic heat exchanger 610 such that the sample tray wells 605 are inserted into the exchanger wells 615, and the contact between the outer surface of the sample tray wells 605 and the inner surface of the exchanger wells 615 is maximized. In addition, surface heaters 620 have been placed upon the sample tray 600, such that the surface heaters 620 are able to heat the sample tray wells 605 from above the sample tray wells 605.

In another embodiment, in place of using sample trays, samples comprising reagents (e.g., PCR reagents) can be held in tubes made of glass or another material capable of efficiently conducting heat and compatible with any reagents to be heated and cooled by the microfluidic heat exchanger. In preferred embodiments, at least a portion of the surface of the sample holder will be made of a material that allows detection of the reaction products, either after the reaction is complete or in real-time, without removal of the sample. For example, real-time PCR relies on the use of fluorescent moities whose emissions, which increase during the course of the reaction, can be detected by a suitable detector. Any methods for detecting the products of PCR reactions taking place in the sample holders, in real-time or otherwise, are known in the art and can be used with the fast thermal cycler of the present invention. Likewise, detection can take place in or out of the sample holders after the reaction is completed (e.g., after thermal cycling is completed).

Thermal Cycling Using Electrical Heating

The thermal cycling system 100 may use complimentary surface heaters to aid in thermal cycling. One or more surface heaters may be used in, for example, the embodiment of FIG. 1, in order to complement the heating of the samples from the fluid flowing through the microfluidic heat exchanger 105. The surface heaters may be integrated or embedded into the top surface of the microfluidic heat exchanger 105, or may be embedded or integrated into the walls of the exchanger wells 110. In one embodiment, the surface heaters are placed over the sample trays when the sample trays are placed upon the microfluidic heat exchanger 105.

The surface heaters may include electrical filament, wiring, resistive tape, or any other material which produces heat from electrical current. Alternatively, any other type of surface heaters may be used, but the remainder of this description will be limited to electrical resistive heaters. The surface heaters may form a single conduit which encircles the top of each exchanger well 110, allowing a single electrical current to be run through the conduit while producing heat for each individual exchanger well 100, and allowing for the unobstructed optical monitoring of the fluorescence of samples throughout the thermal cycling process from above the sample tray wells.

In one embodiment, the switching controller 160 controls the activation of the surface heaters. The switching controller 160 may synchronize the switching of the position of the valve 140 with the activation and deactivation of the surface heaters. For example, when the switching controller 160 switches the position of the valve 140 such that the direction of the fluid flowing through the porous medium 115 switches to fluid flowing from the hot tank 130 through the porous medium 115 and to the cold tank 120, the switching controller 160 activates the surface heaters. In such an embodiment, the samples being thermally cycled are heated by heat transfer from both the fluid flowing through the porous medium 115 and the surface heaters. In this embodiment, when the switching controller 160 switches the position of the valve 140 such that the direction of the fluid flowing through the porous medium 115 switches to fluid flowing from the cold tank 120 through the porous medium 115 and to the hot tank 130, the switching controller deactivates the surface heaters. Thus, the surface heaters complement the fluid flowing through the porous medium 115 only in heating the samples being thermally cycled, while only the fluid flowing through the porous medium 115 cools the samples.

In one embodiment, the switching controller 160 staggers the activation of the surface heaters with the flowing of fluid through the porous medium 115 from the hot tank 130 in the direction of the cold tank 120. For example, the switching controller 160 may activate or deactivate the surface heaters immediately before or after switching the valve 140.

In one embodiment, the switching controller 160 utilizes cascaded PID controllers in conjunction with tape heater surface heaters to control the surface heaters. In this embodiment, a first PID controller interfaces with the tape heaters through a second PID controller. The first PID controller assigns the tape heater a temperature threshold and the second PID controller manages the power required for the tape heaters to reach the temperature threshold. The switching controller 160 may manually adjust the temperature thresholds in real-time as needed. The surface heater temperature thresholds may be independent of or may be based on T1, T2, T3, T4, T5, and T6. In one embodiment, the temperature thresholds are based on the conductivity of the sample trays, or based on the maximum temperature capacity of the sample trays (for instance, the maximum temperature at which the sample trays can be exposed before damage is done to the sample trays).

In addition to surface heaters, the thermal cycling system 100 may use internal heaters to aid in thermal cycling. The internal heaters may be located within the microfluidic heat exchanger 105, for instance within the porous medium 115. The internal heaters may be located under the exchanger wells 110 or around the exchanger wells 110 within the microfluidic heat exchanger 105. The internal heaters may be any type of electrical heater, and, in a manner similar to the surface heaters discussed above, may be controlled by the switching controller 160.

Figure 7:
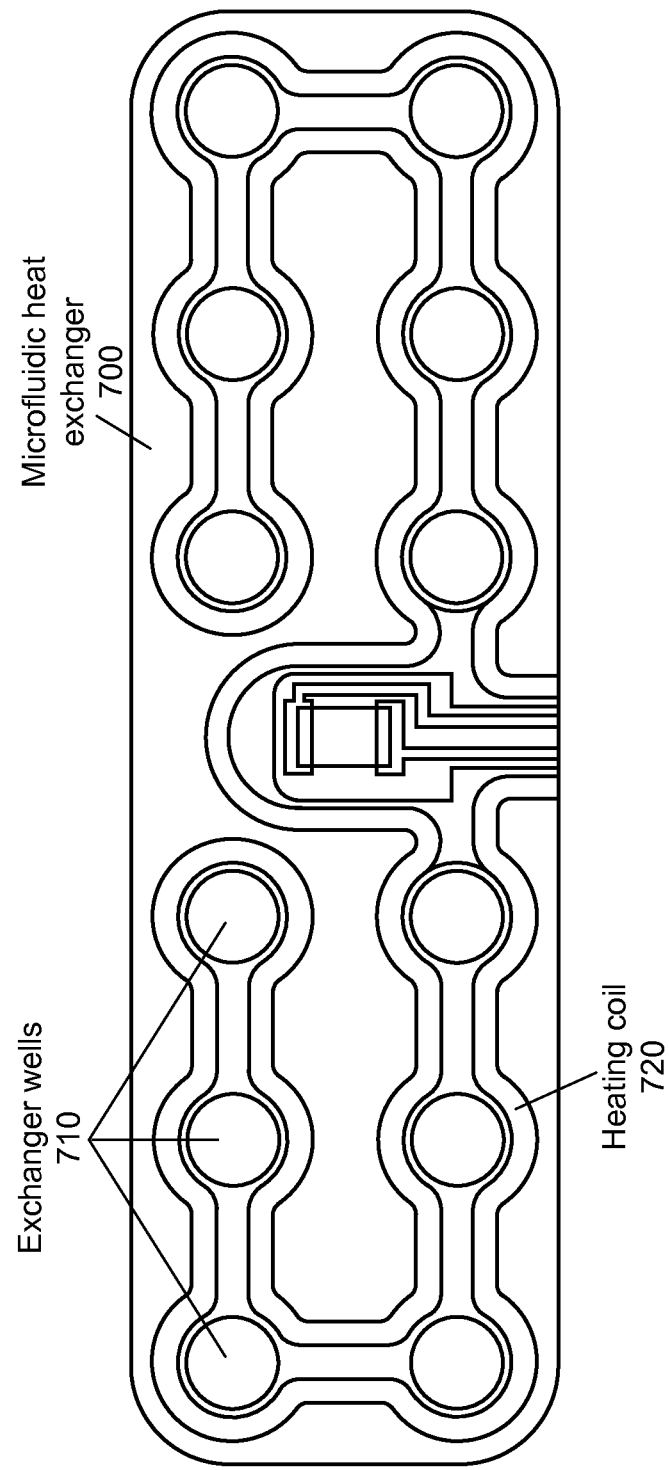
FIG. 7 illustrates a cutaway top view of a microfluidic heat exchanger with internal sample well heating coils in accordance with one embodiment.

FIG. 7 illustrates a cutaway top view of a microfluidic heat exchanger with internal sample well heating coils in accordance with one embodiment. In the embodiment of FIG. 7, the microfluidic heat exchanger 700 has 12 exchanger wells 710. A heating coil 720 partially encircles each exchanger well 710. The heating coil 720 may be a wire or a thermal metallic trace on a flexible circuit which produces resistive heat when electrical current is run through the heating coil 720. The heat produced by the heating coil 720 heats the walls of the exchanger wells 710 and, through heat exchange, the samples contained with the exchanger wells 710. In one embodiment, both the internal heaters and the surface heaters produce heat for intervals of approximately 2 seconds, using approximately 0.5 W of power.

It should be noted that in alternative embodiments, the number and configuration of exchanger wells 710 differs from that illustrated in FIG. 7. For example, the microfluidic heat exchanger 700 may have 16 exchanger wells 710, arranged in a 4×4 configuration. In this embodiment, the heating coil 720 may be configured to surround all or part of each interior well, and/or the interior wells may receive heat through heat exchange from the surrounding wells. This arrangement may beneficially provide heat uniformly from a combination of surrounding wells and the heating coil 720.

The use of internal heaters and surface heaters may allow for greater control of thermal set points in each temperature cycle. For example, in heating the samples in the exchanger wells 110, the heaters may sequentially heat the samples to temperatures T1, T2, . . . , Tk, where T1<T2< . . . <Tk. Heating a sample to a particular temperature, holding the sample at that temperature, and then heating the sample to a higher particular temperature may be required by a thermal cycling protocol. For example, a PCR assay may require a 2- or 3-step procedure, where the PCR sample is heated to a first temperature, then heated to a second temperature, and then to a third temperature (if required). The use of internal and/or surface heaters may beneficially allow the thermal cycling system 100 to heat the samples to these temperatures with a greater accuracy.

In one embodiment, instead of heating samples using fluid flowing from the hot tank 130, the thermal cycling system 100 heats the samples exclusively using surface and/or internal heaters. In this embodiment, the thermal cycling system 100 cools the samples using fluid flowing from the cold tank 120 through the microfluidic heat exchanger 105. Effectively, the surface and/or internal heaters preempt the need for two separate fluid tanks Thus, in one embodiment, the thermal cycling system 100 only includes one tank for providing cooling functionality. In such an embodiment, when the valve 140 is in a first position, fluid flows from the tank through the porous medium 115 and into the reservoir 150, cooling the samples in the exchanger wells 110. Likewise, when the valve 140 is in a second position, fluid does not flow through the porous medium and instead the samples are heated using the surface and/or internal heaters.

In an alternative embodiment, the thermal cycling system 100 may be implemented without a valve 140. In this embodiment, the thermal cycling system 100 heats the samples using surface and/or internal heaters and cools the samples using fluid flowing from the cold tank 120 through the microfluidic heat exchanger 105. In such an embodiment, fluid starts flowing through the cold tank 120 into the microfluidic heat exchanger 105 when the pump 145 is activated and stops flowing when the pump 145 is deactivated. The activation of the surface and/or internal heaters may be synchronized with the deactivation of the pump 145, and vice versa.

Reagents for PCR

As noted above, the various embodiments of the fast thermal cycling apparatus described herein may be used to carry out PCR reactions. The general principle of the PCR reaction is well-known. The fast thermal cycling apparati of the invention can be used with various kits and enzymes including, e.g., SpeedSTAR™ HS DNA Polymerase (Takara Bio Inc.), KAPA2G Fast PCR enzyme (KAPA Biosystems) and others. The operator of the apparatus can use the controller to adjust various parameters (e.g., cycle length, number of cycles, annealing temperature, denaturing temperature, etc.) as desired to optimize the reaction efficiency and/or rate depending on the properties of the enzyme and/or reagents employed and/or the template being investigated.

A number of embodiments of the invention have been described. Nevertheless, it will be understood that various modifications may be made without departing from the spirit and scope of the invention. All publications, patents and other references mentioned herein are hereby incorporated by reference in their entirety.

EXAMPLE 1

The following Example describes a fast thermal cycler apparatus and a demonstration of ultra-fast PCR using the apparatus.

Materials and Methods

PCR Insert.

Unamplified PCR mix was pipetted into an in-house, 6-well (5 µL/well) polypropylene insert (inset in FIG. 1) and covered with a conventional PCR adhesive seal (PN: 48461, Edge BioSystems). Each insert contained two rows of positive template mix separated by a row of negative template control mix. The insert was placed into matching 5 µL wells on the thermal block and covered with the electric heating assembly.

System Architecture:

The ultra-fast PCR instrument is shown schematically in FIG. 2. The system exhibits maximum heating and cooling rates of 45° C./sec, allowing extremely short cycles. The realized thermal time constants associated with the heating and cooling ramps of a single cycle are approximately 1.02 seconds and 1.32 seconds respectively. The largest thermal resistance in the system is the polypropylene insert (sample holder). The thermal block was fabricated from copper with a porous foam structure on the underside and placed in a sealed fluidics package. Flow through the package was achieved by means of a pump (PN: ML-75211-62, Cole Parmer) connected to inlet and exhaust valves (PN: 8300A082U, ASCO Valve Inc.) that directed reservoir fluid through heating or cooling coils. The coils were submerged in water-filled hot and cold circulator baths (PN: MK-12121-40, Cole-Parmer) maintained at approximately 98° C. and 30° C., respectively. A LabVIEW-based controller monitored the thermal block temperature as reported by a 0.010-in. type-K insulated thermocouple (PN: 5TC-TT-K-36-36, Omega Engineering) in real-time and activated the inlet and exhaust valves to achieve the desired two-step thermal profile for each cycle. Additional heating capacity was provided by the electric heating assembly, which consisted of an in-house 28.94-Ω flexible nichrome resistive heating element covered with copper and controlled through a Watlow Series 96 temperature controller.

PCR Reagents.

A PCR mastermix was made for each enzyme/template combination based upon a standard reaction volume of 25 µL. Once made, 5 µL of the mastermix/template mixture was aliquoted per well on the insert. Single reactions were performed in 5 µL wells.

Rapid PCR reactions were performed by testing two separate PCR enzyme kits: SpeedSTAR™ HS DNA Polymerase (Takara Bio Inc.) and KAPA2G Fast PCR enzyme (KAPA Biosystems). The manufacturer recommended PCR chemistries were followed with the exception of an increased concentration of PCR enzyme for the Speedstar™ HS DNA Polymerase mix.

SpeedSTAR™ HS DNA Polymerase was used to amplify a 58 base pair (bp) *Erwinia herbicola* target as well as a 107 bp SARS target. Reactions to amplify the 58 bp *Erwinia herbicola* target with SpeedSTAR™ HS DNA polymerase included 2.5 µL SpeedSTAR™ 10× Fast Buffer I (which provided a final $MgCl_2$ concentration of 3 mM), 0.2 µM dNTP (each) (NEB), 0.4 µM Eh forward primer 5'-GCTG-CAAAACGCACAACA-3' (SEQ ID NO: 1), 0.4 µM Eh reverse 5'-CGTGAACAAACGGCTCCA-3' (SEQ ID NO: 2), 1.25 U SpeedSTAR™ HS DNA Polymerase, and was brought to 20 µL with RT-PCR grade water (Ambion). Five µL of template (1 ng/µL Eh genomic DNA, ATCC) was added per 20 µL reaction volume. The SARS SpeedSTAR™ HS DNA polymerase reactions included 2.5 µL SpeedSTAR™ 10× Fast Buffer I (3 mM $MgCl_2$), 0.2 µM dNTP (each), 0.4 µM SARS forward primer 5'-TGCCTTCCT-CATCCTTCTCC-3' (SEQ ID NO: 3), 0.4 µM SARS reverse 5'-TGATGTCGTCTACAGGGCTTTT-3' (SEQ ID NO: 4), 1.25 U SpeedSTAR HS DNA Polymerase, brought to 20 µL with RT-PCR grade water. Five µL of 1.418 fg/µL template (193 bp SARS sequence, synthetic oligomer from Biosearch) was added per 20 µL reaction volume.

KAPA2G Fast PCR enzyme was used to amplify a 58 bp target and a 160 bp target in *Erwinia herbicola*. KAPA2G Fast reactions to amplify the 58 bp *Erwinia herbicola* target were made as follows: 5 µL 5×KAPA2G Buffer A (which provided a final $MgCl_2$ concentration of 1.5 mM), 0.2 µM each dNTP, 0.4 µM Eh forward primer 5'-GCTG-CAAAACGCACAACA-3' (SEQ ID NO: 5), 0.4 µM Eh reverse 5'-CGTGAACAAACGGCTCCA-3' (SEQ ID NO: 6), 1 U KAPA2G Fast DNA Polymerase. The total volume was brought up to 20 µL with RT-PCR Grade water, and 5 µL template (1 ng/µL Eh genomic DNA), was added per 20 µL reaction volume. KAPA2G Fast reactions to amplify the 160 bp Eh target included 5 µL 5×KAPA2G Buffer A, 0.2 µM dNTP (each), 0.4 µM Eh forward primer 5'-GCTG-CAAAACGCACAACA-3' (SEQ ID NO: 7), 0.4 µM Eh reverse 5'-GTCTGGTCTCGGTCAGA-3' (SEQ ID NO: 8), 1 U KAPA2G Fast DNA polymerase, brought to 20 µL with RT-PCR grade water. Five µL of template (1 ng/µL Eh genomic DNA) was added per 20 µL reaction volume.

Benchtop positive controls were amplified on a Biorad DNA Engine. The benchtop thermal profile consisted of 30 cycles of 1 second at 95° C. followed by 1 second at 50° C. With the fastest possible ramp rates the benchtop thermal profile required 38 minutes to complete. Five µL of PCR mix was amplified in a 200 µL thin walled tube (Axygen). To prevent evaporation, 5 µL of PCR grade mineral oil (Sigma) was placed on top of the PCR mix. All amplified products were analyzed by mixing 5 µL of product with 12 µL of RT-PCR grade water and then loading 17 µL onto a 4% agarose E-Gel® (Invitrogen) run in an E-gel® base (Invitrogen) for 15-20 minutes. A 25 bp DNA ladder (Invitrogen) was used for confirmation of product size.

Instrument Cycling Parameters.

A variety of cycling parameters were tested on the instrument. A gradient of upper block target temperatures was tested ranging from 88-92° C. while the lower target temperatures ranged from 45-55° C., depending on the assay. Experiments were also performed both with and without a 5 second hotstart. Variations in cycling numbers, 30 or 35 cycles were also tested depending on the PCR assay.

Sample recovery from the 6-well inserts required using a 1 cc insulin syringe (Becton-Dickinson) to pierce the well and withdraw the product. Each collected sample (~5 µL) was brought to a final volume of 174 with RT-PCR Grade water. The sample/water mixture was loaded onto a 4% agarose gel and ran for 15-20 minutes. A 25 bp DNA ladder was used for confirmation of product size.

Results

Figure 9:
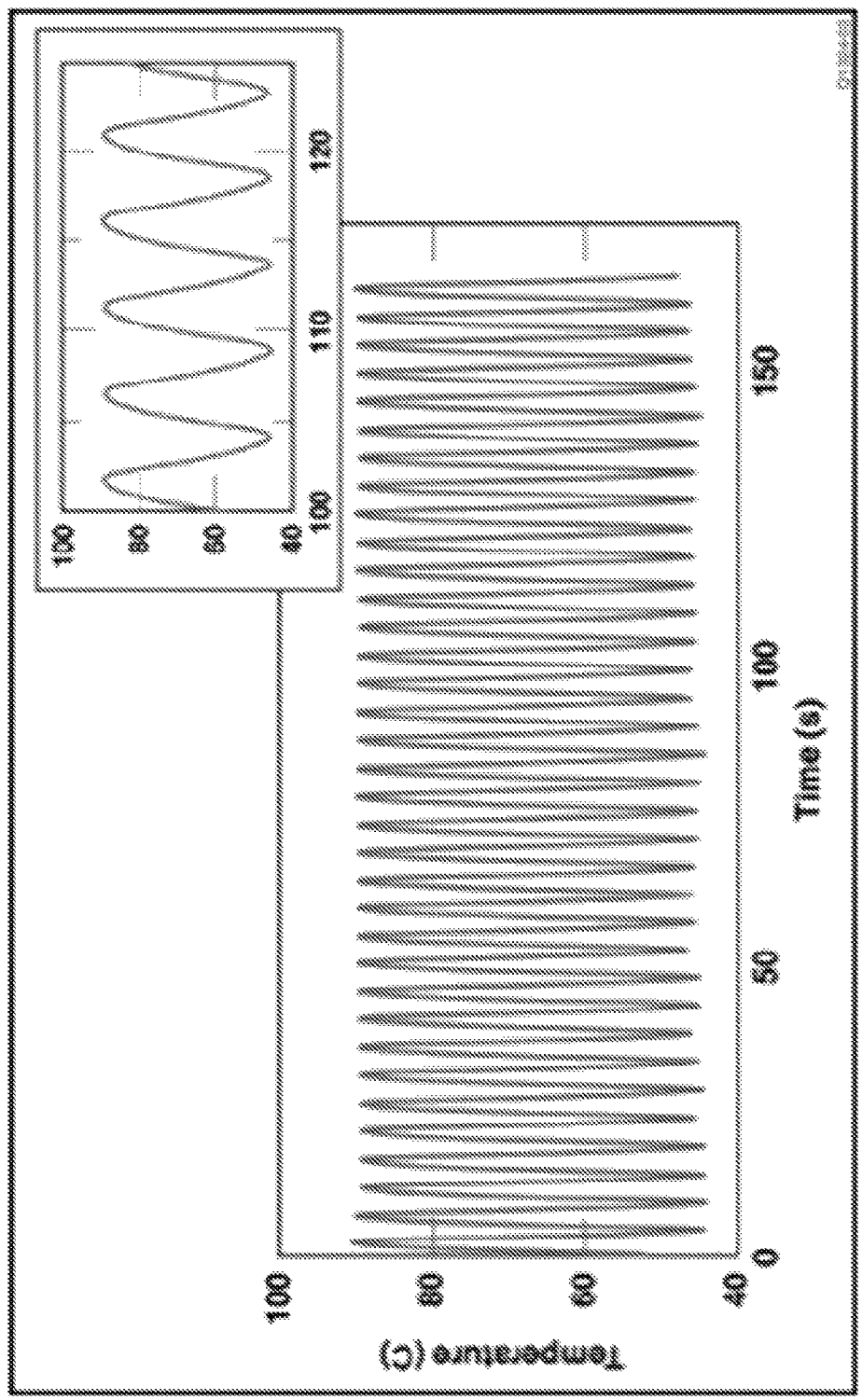
FIG. 9 is a thermal trace showing 35 cycles in 2:46 with inset showing an expanded view of a few cycles with an average cycle time of 4.7 seconds. Average values with standard deviation are 89.64±0.33 for denaturation temperature and 45.39±0.65 for annealing temperature.

For a typical PCR reaction 30 to 40 repetitions of thermal cycling between the annealing and denaturation temperature (55° C. and 94° C., respectively) are required. FIG. 9 shows the thermal trace generated for a typical 35-cycle experiment. The total time for this PCR run was 2 minutes and 46 seconds. The inset in FIG. 9 shows an expanded view for a couple of cycles with an average cycle time of 4.7 seconds. During instrument calibration, a less than two-degree difference was measured between the block temperature and the temperature of the liquid within the well due to the polymer interface. For the trace in FIG. 9, the standard deviation was 0.65 for annealing versus only 0.33 for denaturation, probably due to the thermal gradient positional effects between the block and lid at the thermocouple measurement location during the cooling phase. Agarose gel analysis of the results of two different PCR reaction showed that that the reactions were specific, i.e., one band was visible for each amplicon. Although the bands were not as bright as standard benchtop cyclers, the results showed that amplification was achieved in less than 3:00.

Table 1 shows that a variety of template and enzyme combinations can be amplified under 3 minutes using the ultra-fast thermal cycling apparatus. Amplification specificity for all runs represented in Table 1 was confirmed by agarose gel. While the enzymes listed here were able to show amplification at these fast times, this should not be interpreted as an exclusive list of fast enzymes. One skilled in the art will be able to identify other existing enzymes suitable for ultra-fast PCR. For example, KOD has been tested and shown to support very rapid amplification by Maltezos et al. (Maltezos et al., *Appl. Phys. Lett.* (2010) 97, 264101).

TABLE 1

PCR reactions under 3 minutes for various amplicon sizes, greater than 9 replicates for each combination. Enzyme mix/template mixes in bold italics have been tested and support amplification in under 2½ minutes (2:18).

| | Template | |
|---|---|---|
| Enzyme/Mix | SARS | *Erwinia herbicola* |
| SpeedSTAR ™ | 107 bp | 58 bp |
| KAPA2G | | *58 bp*  *160 bp* |
| Fastest time in sub-3 minute range | 2:46 | 2:18   2:18 |
| Average time in sub-3 minute range | 2:52 ± :04 (N = 11) | 2:44 ± :11   2:47 ± :11 (N = 29)   (N = 10) |

Compared to benchtop instruments or traditional thermal cycling protocols the total amplification time is dramatically reduced even though the apparatus operated on 5 µL volumes. For a typical 30-cycle amplification, the average cycle time is 5.6 seconds or less. Table 2 summarizes the different cycling parameters that ultra-fast PCR apparatus experiences relative to the standard bench top thermal cycler and a commercially available fast PCR device.

TABLE 2

Comparison of Fast PCR to other PCR devices (na = information not available)

| | Fast PCR Device | | | Benchtop PCR device | COTS fast thermal cycler[4] |
|---|---|---|---|---|---|
| Total PCR time (min:s) | 2:23 ± 0.05 | 2:50 ± 0.08 | 2:50 ± 0.04 | 38 | 10 |
| # cycles | 30 | 30 | 35 | 30 | 25 |
| Annealing time (s) | 0.82 ± 0.08 | 1.43 ± 0.56 | 0.84 ± 0.02 | 1 | na |

TABLE 2-continued

Comparison of Fast PCR to other PCR devices (na = information not available)

|  | Fast PCR Device | | | Benchtop PCR device | COTS fast thermal cycler[4] |
| --- | --- | --- | --- | --- | --- |
| Extension time (s) | 0.44 ± 0.02 | 0.38 ± 0.09 | 0.44 ± 0.02 | 1 | na |
| Ave cycle time (s) | 4.71 ± 0.17 | 5.55 ± 0.25 | 4.4 ± 1.39 | 76 | 24 |
| N | 5 | 21 | 23 | | |

The annealing time in Table 2 was defined as the time that the block temperature was at or below 50° C. The extension time was conservatively defined as the time that the block temperature was greater than or equal to 70° C. and less than or equal to 80° C. In reality the polymerase will begin extending the amplicon as soon as the primer anneals. For successful fast PCR of ≤160 bp amplicons, the annealing temperature is more critical than the extension time. For longer amplicons, a short length-dependent extension hold may be helpful, although most genetic identification applications are well served with amplicon sizes less than 160 bp.

Additional Considerations

Reference in the specification to "one embodiment" or to "an embodiment" means that a particular feature, structure, or characteristic described in connection with the embodiments is included in at least one embodiment. The appearances of the phrase "in one embodiment" or "an embodiment" in various places in the specification are not necessarily all referring to the same embodiment.

In addition, the language used in the specification has been principally selected for readability and instructional purposes, and may not have been selected to delineate or circumscribe the inventive subject matter. Accordingly, the disclosure is intended to be illustrative, but not limiting, of the scope of the embodiments.

While particular embodiments and applications have been illustrated and described herein, it is to be understood that the embodiment is not limited to the precise construction and components disclosed herein and that various modifications, changes, and variations may be made in the arrangement, operation, and details of the methods and apparatuses without departing from the spirit and scope.

What is claimed is:

1. An apparatus for thermally cycling a material, comprising:
   a microfluidic heat exchanger comprising one or more wells for receiving one or more samples to be thermally cycled and further comprising a porous medium, a first inlet channel, and a second inlet channel;
   a tank for holding fluid at a first temperature, the tank coupled to the first inlet channel and the second inlet channel of the microfluidic heat exchanger;
   an electric heater thermally coupled to a top surface of the microfluidic heat exchanger;
   a pump coupled to the tank; and
   a controller configured to alternatively configure the apparatus into a heating mode and a cooling mode, wherein the controller is configured to deactivate the electric heater and activate the pump such that the pump pumps fluid from the tank through the first inlet into the porous medium and from the porous medium through the second inlet into the tank when the apparatus is configured in the cooling mode, and wherein the controller is configured to deactivate the pump and activate the electric heater to a second temperature greater than the first temperature when the apparatus is configured in the heating mode.

2. The apparatus of claim 1, further comprising:
a temperature sensor coupled to the microfluidic heat exchanger and the controller, the temperature sensor configured to determine the temperature of the one or more samples contained within the microfluidic heat exchanger wells and to communicate the determined temperature to the controller.

3. The apparatus of claim 2, wherein the controller is configured to configure the apparatus into the heating mode in response to a determination that the determined temperature of the one or more samples received from the temperature sensor falls below a first temperature threshold.

4. The apparatus of claim 2, wherein the controller is configured to configure the apparatus into the cooling mode in response to a determination that the determined temperature of the one or more samples received from the temperature sensor exceeds a second temperature threshold.

5. The apparatus of claim 1, wherein the microfluidic heat exchanger is configured to receive a sample tray, the sample tray comprising one or more wells, and wherein the sample tray wells are inserted into the microfluidic heat exchanger wells when the sample tray is placed upon the microfluidic heat exchanger.

6. The apparatus of claim 5, wherein the sample tray comprises a sample tray lid configured to seal the sample tray wells, and wherein the electric heater abuts the sample tray lid.

7. The apparatus of claim 1, wherein the electric heater comprises a heating coil at least partially surrounding a perimeter of each well of the microfluidic heat exchanger.

8. The apparatus of claim 7, wherein the heating coil comprises a thermal metallic trace configured to produce resistive heat when electric current flows through the thermal metallic trace.

9. The apparatus of claim 1, wherein the controller is configured to alternately cycle the apparatus from the cooling mode to the heating mode and back to the cooling mode for 30 or more cycles.

10. The apparatus of claim 9, wherein, for a given cycle, the apparatus is configured in the heating mode for a longer duration of time than the apparatus is configured in the cooling mode.

11. An apparatus for thermally cycling a material, comprising:
a microfluidic heat exchanger comprising one or more wells for receiving one or more samples to be thermally cycled and further comprising a porous medium, a first inlet channel, and a second inlet channel;
a tank for holding fluid at a first temperature, the tank coupled to the first inlet channel and the second inlet channel of the microfluidic heat exchanger;
an electric heater located within the porous medium of the microfluidic heat exchanger;
a pump coupled to the tank; and
a controller configured to alternatively configure the apparatus into a heating mode and a cooling mode, wherein the controller is configured to deactivate the electric heater and activate the pump such that the pump pumps fluid from the tank through the first inlet into the porous medium and from the porous medium through the second inlet into the tank when the apparatus is configured in the cooling mode, and wherein the controller is configured to deactivate the pump and activate the electric heater to a second temperature greater than the first temperature when the apparatus is configured in the heating mode.

12. The apparatus of claim 11, further comprising:
a temperature sensor coupled to the microfluidic heat exchanger and the controller, the temperature sensor configured to determine the temperature of the one or more samples contained within the microfluidic heat exchanger wells and to communicate the determined temperature to the controller.

13. The apparatus of claim 12, wherein the controller is configured to configure the apparatus into the heating mode in response to a determination that the determined temperature of the one or more samples received from the temperature sensor falls below a first temperature threshold.

14. The apparatus of claim 12, wherein the controller is configured to configure the apparatus into the cooling mode in response to a determination that the determined temperature of the one or more samples received from the temperature sensor exceeds a second temperature threshold.

15. The apparatus of claim 11, wherein the microfluidic heat exchanger is configured to receive a sample tray, the sample tray comprising one or more wells, and wherein the sample tray wells are inserted into the microfluidic heat exchanger wells when the sample tray is placed upon the microfluidic heat exchanger.

16. The apparatus of claim 11, wherein the electric heater comprises a heating coil located underneath each well of the microfluidic heat exchanger.

17. The apparatus of claim 11, wherein the electric heater comprises a heating coil located around each well of the microfluidic heat exchanger and at least partially surrounding a perimeter of each well of the microfluidic heat exchanger.

18. The apparatus of claim 17, wherein the heating coil comprises a thermal metallic trace configured to produce resistive heat when electric current flows through the thermal metallic trace.

19. The apparatus of claim 11, wherein the controller is configured to alternately cycle the apparatus from the cooling mode to the heating mode and back to the cooling mode for 30 or more cycles.

20. The apparatus of claim 19, wherein, for a given cycle, the apparatus is configured in the heating mode for a longer duration of time than the apparatus is configured in the cooling mode.

* * * * *

SEQUENCE LISTING

```
<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gctgcaaaac gcacaaca                                                 18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgtgaacaaa cggctcca                                                 18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgccttcctc atccttctcc                                               20

<210> SEQ ID NO 4
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgatgtcgtc tacagggctt tt                                              22

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctgcaaaac gcacaaca                                                   18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgtgaacaaa cggctcca                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctgcaaaac gcacaaca                                                   18

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtctggtctc ggtcaga                                                    17
```